(12) United States Patent
Ochi et al.

(10) Patent No.: US 12,096,918 B2
(45) Date of Patent: Sep. 24, 2024

(54) IMAGING NEEDLE SYSTEM AND APPARATUS WITH LIGHT ENGINE

(71) Applicant: NanoSurgery Technology Corporation, Sarasota, FL (US)

(72) Inventors: Sam Seiichiro Ochi, Lakewood Ranch, FL (US); Mark Walter, Sarasota, FL (US); David Martin, Sarasota, FL (US)

(73) Assignee: NanoSurgery Technology Corporation, Sarasota, FL (US)

( * ) Notice: Subject to any disclaimer, the term of this patent is extended or adjusted under 35 U.S.C. 154(b) by 0 days.

(21) Appl. No.: 16/997,783

(22) Filed: Aug. 19, 2020

(65) Prior Publication Data

US 2021/0052152 A1 Feb. 25, 2021

Related U.S. Application Data

(60) Provisional application No. 62/924,599, filed on Oct. 22, 2019, provisional application No. 62/904,252, (Continued)

(51) Int. Cl.
*A61B 1/00* (2006.01)
*A61B 1/015* (2006.01)
(Continued)

(52) U.S. Cl.
CPC .......... *A61B 1/317* (2013.01); *A61B 1/00078* (2013.01); *A61B 1/00108* (2013.01);
(Continued)

(58) Field of Classification Search
CPC . A61B 1/317; A61B 1/00078; A61B 1/00108; A61B 1/00128; A61B 1/00154;
(Continued)

(56) References Cited

U.S. PATENT DOCUMENTS 5,053,016 A * 10/1991 Lander ............... A61B 17/3498
251/298
5,323,767 A * 6/1994 Lafferty ............... A61B 1/0623
600/109

(Continued)

FOREIGN PATENT DOCUMENTS

WO 2018221014 A1 6/2018
WO WO2018113885 A1 6/2018

OTHER PUBLICATIONS

Search Report and Written Opinion dated Dec. 18, 2020 for PCT Application No. PCT/US2020/047056.

*Primary Examiner* — Timothy J Neal

(57) ABSTRACT

An imaging needle apparatus, associated system, and method of use are described. The apparatus includes various interchangeable modules, including a trocar assembly, a blunt cannula assembly, and an arthroscope assembly, such as a nano-arthroscope. For example, using the imaging needle apparatus, a doctor can treat a patient by inserting the trocar assembly into the patient's body, inserting the blunt cannula assembly into the body via the trocar assembly, removing the trocar assembly, and inserting the arthroscope assembly into the blunt cannula assembly. Further, the imaging needle apparatus, in some embodiments, includes a light engine that provides a light source for a camera cannula of the apparatus, such as a camera cannula that is part of the arthroscope assembly.

19 Claims, 20 Drawing Sheets

Related U.S. Application Data filed on Sep. 23, 2019, provisional application No. 62/888,937, filed on Aug. 19, 2019.

(51) Int. Cl.
| | |
|---|---|
| *A61B 1/05* | (2006.01) |
| *A61B 1/06* | (2006.01) |
| *A61B 1/07* | (2006.01) |
| *A61B 1/317* | (2006.01) |
| *A61B 17/32* | (2006.01) |
| *A61M 3/02* | (2006.01) |
| *A61M 39/24* | (2006.01) |

(52) U.S. Cl.
CPC ...... *A61B 1/00128* (2013.01); *A61B 1/00154* (2013.01); *A61B 1/015* (2013.01); *A61B 1/05* (2013.01); *A61B 1/0607* (2013.01); *A61B 1/0669* (2013.01); *A61B 1/0684* (2013.01); *A61B 1/07* (2013.01); *A61B 17/320016* (2013.01); *A61M 3/0262* (2013.01); *A61B 1/00016* (2013.01); *A61M 2039/244* (2013.01)

(58) Field of Classification Search
CPC ......... A61B 1/015; A61B 1/05; A61B 1/0607; A61B 1/0669; A61B 1/0684; A61B 1/07; A61B 1/00016; A61B 2017/00345; A61B 17/320016; A61B 2017/3454; A61B 17/3421; A61M 3/0262; A61M 2039/244
See application file for complete search history.

(56) References Cited

U.S. PATENT DOCUMENTS

| | | | | |
|---|---|---|---|---|
| 6,902,526 B2 * | 6/2005 | Katzman | ............... | A61B 1/313 600/101 |
| 2003/0042493 A1 | 3/2003 | Kazakevich | | |
| 2003/0181858 A1 * | 9/2003 | Lajtai | ............... | A61B 17/3421 604/167.06 |
| 2004/0082915 A1 * | 4/2004 | Kadan | ............... | A61B 1/00105 604/164.04 |
| 2004/0179789 A1 * | 9/2004 | Shi | ............... | G01J 1/4257 385/33 |
| 2006/0149127 A1 * | 7/2006 | Seddiqui | ............... | A61B 1/0052 600/104 |
| 2007/0167681 A1 * | 7/2007 | Gill | ............... | A61B 1/00059 600/179 |
| 2009/0040754 A1 | 2/2009 | Brukilacchio et al. | | |
| 2009/0318951 A1 | 12/2009 | Kashkarov et al. | | |
| 2011/0122366 A1 * | 5/2011 | Smith | ............... | A61B 1/313 351/221 |
| 2011/0170112 A1 * | 7/2011 | Gibler | ............... | G01J 3/26 356/480 |
| 2012/0041267 A1 | 2/2012 | Benning et al. | | |
| 2012/0203075 A1 * | 8/2012 | Horvath | ............... | A61B 1/07 600/249 |
| 2014/0257332 A1 * | 9/2014 | Zastrozna | ............... | A61B 17/3421 606/130 |
| 2015/0196193 A1 * | 7/2015 | Kienzle | ............... | A61B 1/0676 600/109 |
| 2015/0265466 A1 | 9/2015 | Bhadri et al. | | |
| 2016/0324409 A1 * | 11/2016 | Tabata | ............... | G02B 23/26 |
| 2017/0059763 A1 * | 3/2017 | Lucrecio | ............... | H02J 7/35 |
| 2017/0059848 A1 * | 3/2017 | Haraguchi | ............... | G02B 23/2469 |
| 2017/0078583 A1 * | 3/2017 | Haggerty | ............... | H04N 23/55 |
| 2018/0177386 A1 | 6/2018 | Wortelboer | | |
| 2018/0228346 A1 * | 8/2018 | Sekowski | ............... | A61B 1/0055 |
| 2018/0239124 A1 * | 8/2018 | Naruse | ............... | A61B 1/04 |
| 2019/0038122 A1 | 2/2019 | Kienzle et al. | | |
| 2019/0175300 A1 | 6/2019 | Horn et al. | | |
| 2020/0187340 A1 | 6/2020 | Blondia | | |
| 2021/0282631 A1 * | 9/2021 | Schultheis | ............... | A61B 1/0669 |
| 2021/0290039 A1 * | 9/2021 | Sekowski | ............... | A61B 1/0055 |
| 2022/0054052 A1 * | 2/2022 | Loach | ............... | G02B 6/4246 |
| 2022/0079625 A1 * | 3/2022 | Einarsson | ............... | A61B 1/00096 |
| 2022/0095896 A1 * | 3/2022 | Hanano | ............... | G02B 6/0008 |

* cited by examiner

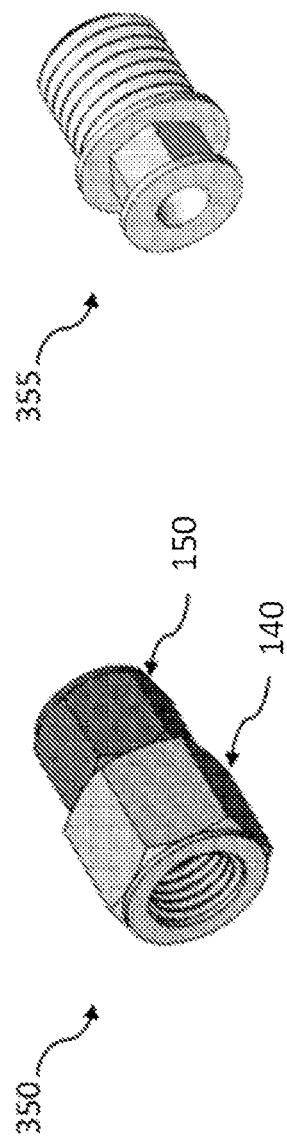

380

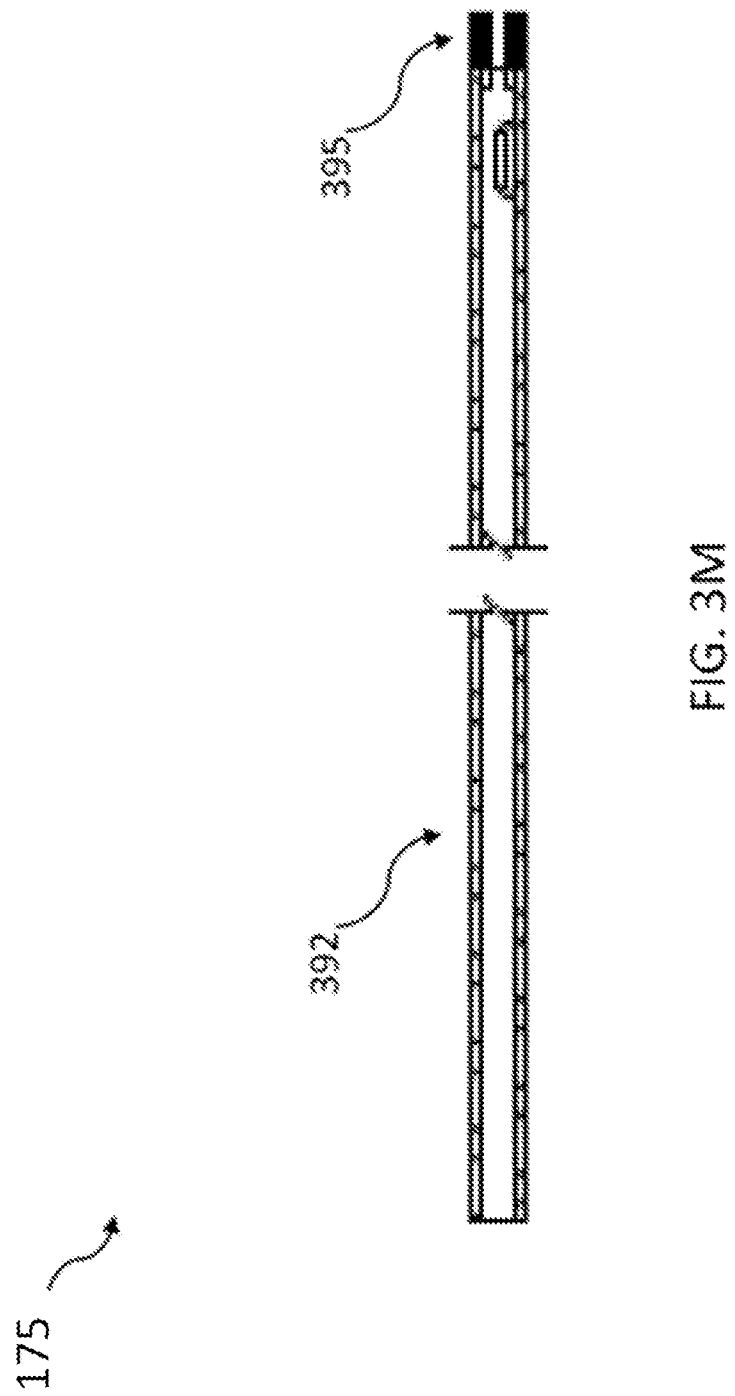

IMAGING NEEDLE SYSTEM AND APPARATUS WITH LIGHT ENGINE

CROSS REFERENCE TO RELATED APPLICATIONS

This application claims priority to U.S. Provisional Patent Application No. 62/888,937, filed on Aug. 19, 2019, entitled VIDEO SCOPE SYSTEM, U.S. Provisional Patent Application No. 62/904,252, filed on Sep. 23, 2019, entitled IMAGING NEEDLE SYSTEM WITH LIGHT ENGINE, and U.S. Provisional Patent Application No. 62/924,599, filed on Oct. 22, 2019, entitled IMAGING NEEDLE SYSTEM WITH LIGHT ENGINE, all of which are hereby incorporated by reference in their entirety.

BACKGROUND

Traditional surgical procedures are typically open procedures. In an open surgical procedure, a surgeon makes a large incision on a patient in order to view and correct physical ailments using surgical tools. Open procedures have several drawbacks. The large surgical incisions used to perform open procedures can become infected. Surgeons may damage surrounding tissues during open procedures, while trying to manipulate the surgical site. Open procedures often require patients to undergo full anesthesia, which independently increases risks of death and/or serious complications. In addition, open procedures can cause patients severe discomfort during recovery periods.

In order to avoid the complications of open procedures, surgeons have developed minimally invasive surgical techniques to perform surgeries that were traditionally performed as open procedures. In contrast to open procedures, minimally invasive procedures can be performed by inserting surgical tools through small incisions in a patient's skin. Minimally invasive procedures have various advantages over open procedures, including lower infection risks, lower patient discomfort, and lower anesthesia requirements.

The small incisions used in minimally invasive procedures make viewing the surgical field difficult. Accordingly, surgeons generally use imaging devices, such as endoscopes, during the minimally invasive procedures in order to indirectly view the surgical field. Often, these imaging devices are inserted into a patient's body through the small incisions.

Arthroscopy is a type of minimally invasive orthopedic procedure performed in a skeletal joint cavity. An arthroscope includes a camera that may be inserted directly into a skeletal joint. With help from the arthroscope, surgeons can diagnose various problems related to the skeletal joint.

In certain cases, arthroscopes can be used to determine whether a therapeutic material should be delivered to the skeletal joint. For example, a surgeon may use an arthroscope to determine whether to deliver a drug, stem cells, or anesthesia for a future procedure to the skeletal joint. Some of these therapeutic materials can be injected using a syringe and a needle.

The cameras used in medical applications, such as those used in arthroscopes, should be precise and have high resolution. However, traditional high-resolution imaging modalities may be expensive. Furthermore, these imaging modalities may be bulky and/or unsuitable for certain applications. These and other problems exist with respect to using conventional arthroscopes.

BRIEF DESCRIPTION OF THE DRAWINGS

FIGS. 3A-3M are diagrams illustrating various components of the imaging needle apparatus.

Figure 1A:
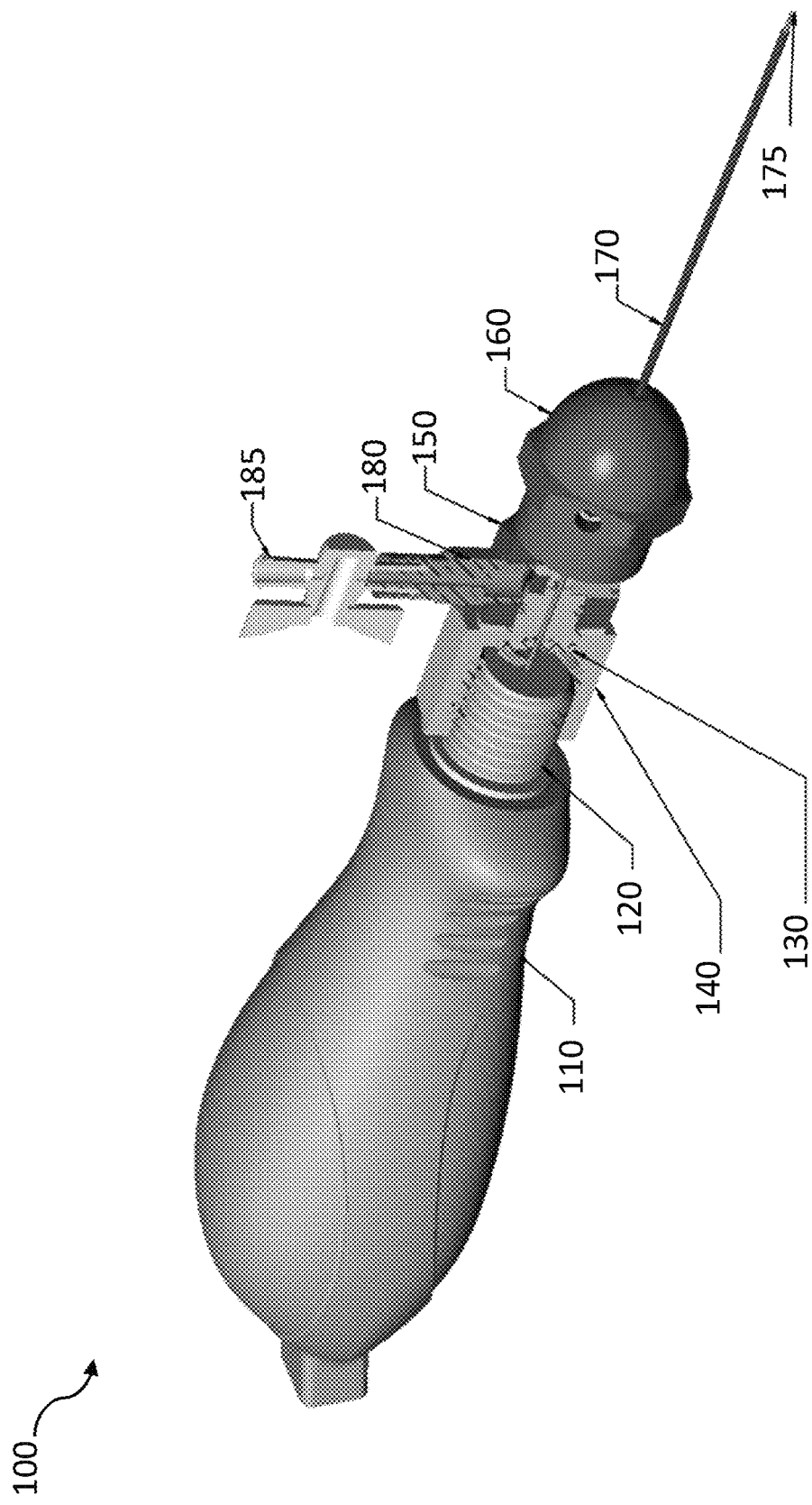
FIGS. 1A-1B are diagrams illustrating an imaging needle apparatus and associated system.

In the drawings, some components are not drawn to scale, and some components and/or operations can be separated into different blocks or combined into a single block for discussion of some of the implementations of the present technology. Moreover, while the technology is amenable to various modifications and alternative forms, specific implementations have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DETAILED DESCRIPTION

Overview

An imaging needle apparatus, associated system, and method of use are described. The apparatus includes various interchangeable modules, including a trocar assembly, a blunt cannula assembly, and an arthroscope assembly, such as a nano-arthroscope assembly (also called a "nanoscope assembly"), where a nano-arthroscope is a small arthroscope (e.g., having a needle or cannula size of around 18-gauge).

For example, using the imaging needle apparatus, a doctor can treat a patient by inserting the trocar assembly into a cannula assembly, inserting a resulting assembly of the trocar assembly and the blunt cannula assembly into the patient's body, removing the trocar assembly, and inserting the arthroscope assembly into the blunt cannula assembly.

Further, the imaging needle apparatus, in some embodiments, includes a light engine that provides a light source for a camera cannula of the apparatus, such as a camera cannula that is part of the nano-arthroscope assembly. The light engine can include a light emitting device (LED) and various light modifying optical components, and operates to provide an intense, focused beam of light to the arthroscope assembly, such that the nano-arthroscope assembly can provide sufficient illumination for needles having sizes of 21.5-gauge to 18-gauge, or smaller.

Thus, the imaging needle apparatus may be used as an arthroscope for incisions and treatments that utilize an 18 G needle. For example, due to the small size of the imaging components, an arthroscopic procedure can be performed without the use of positive pressure apparatus, unlike procedures using traditional arthroscopes. A doctor, therefore, can utilize the imaging needle apparatus in an office setting, in order to provide a variety of injections, without the potential drawbacks associated with using larger needles, among other benefits.

In the following description, for the purposes of explanation, numerous specific details are set forth in order to provide a thorough understanding of implementations of the present technology. It will be apparent, however, to one skilled in the art that implementations of the present technology can be practiced without some of these specific details. The phrases "in some implementations," "according to some implementations," "in the implementations shown," "in other implementations," and the like generally mean the particular feature, structure, or characteristic following the phrase is included in at least one implementation of the present technology and can be included in more than one implementation. In addition, such phrases do not necessarily refer to the same implementations or different implementations.

Examples of the Imaging Needle Apparatus

Figure 1B:
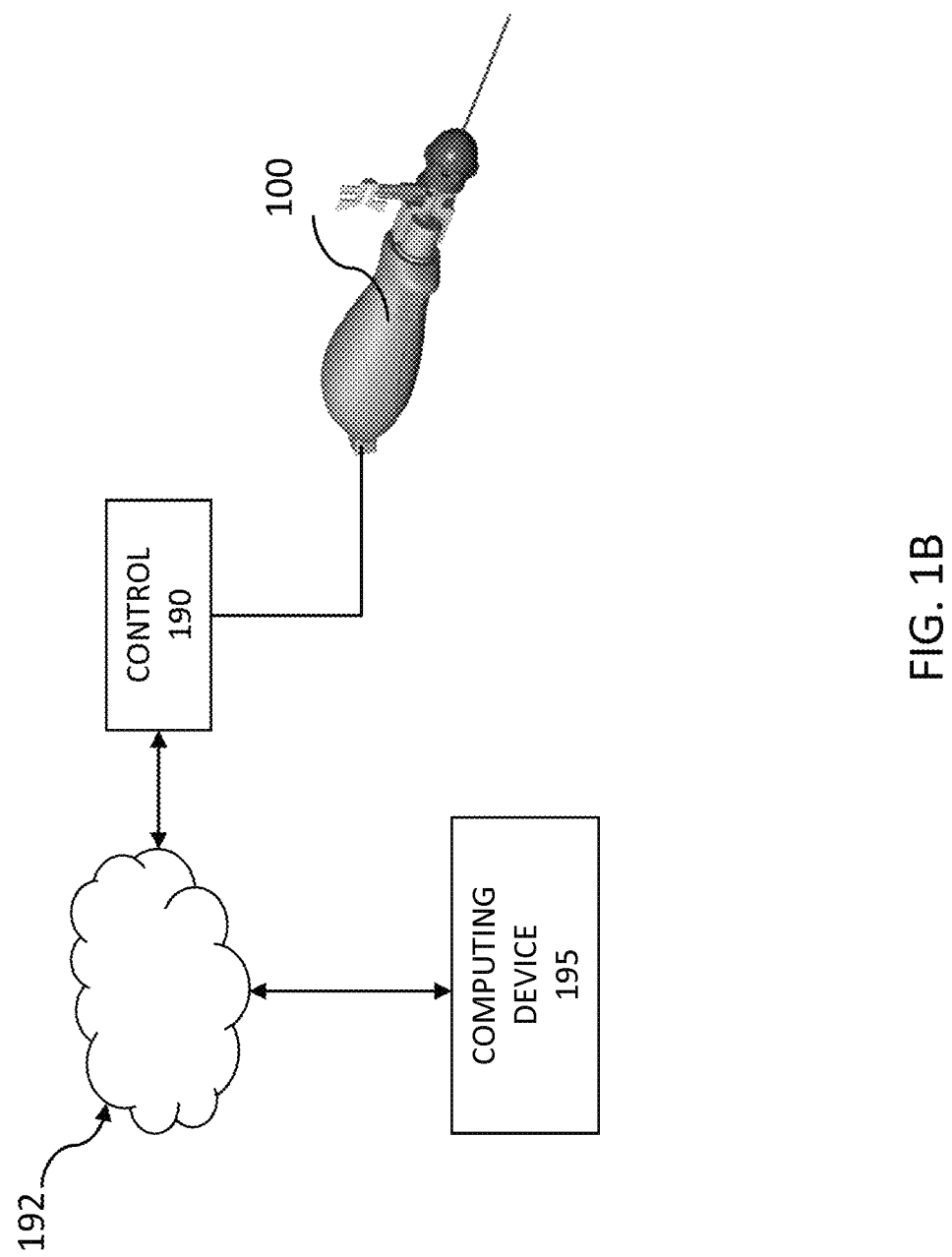

FIGS. 1A-1B are diagrams illustrating an imaging needle apparatus 100 and associated system. Referring to FIG. 1A, the imaging needle apparatus 100 includes a housing or handpiece 110, which contains a light engine and optional control components (not shown). The handpiece 110 attaches via an adapter 120, screwing into a proximal hex adjuster 140 and inner compression plate 130, such as an O ring.

The proximal hex adjuster 140 mates with a distal hex adjuster 150, which receives a cannula adapter 160, configured to attach an outer cannula 170 to the apparatus. Within the outer cannula 170 is a camera cannula 175, which, as described herein, includes imaging and lighting components at a tip portion of the cannula body.

Further, the imaging needle apparatus 100 includes a quick turn plug luer 180 and luer stopcock 185, which facilitate the attachment of a syringe (not shown) to the apparatus 100. By attaching a syringe via the luer 180, the apparatus can facilitate the injecting of fluids or other materials via the outer cannula 170 while also utilizing the camera cannula 175 to image and view the cavity within the body being treated.

FIG. 1B depicts the imaging needle apparatus 100 within a network environment. The imaging needle apparatus is coupled to a control device 190, which operates to control various functions of the apparatus 100, including the camera cannula 175 and its imaging and lighting components. For example, the control device 190 can control (e.g., vary) an intensity of light used during a procedure, while also controlling the recording of images or video within the field of view of the imaging components during the procedure.

While FIG. 1B depicts the control device 190 as being a separate component from the imaging needle apparatus 100, in some cases, some or all components of the control device 190 can be integrated into the apparatus 100, such as within the handpiece or housing 110. For example, the handpiece 110 can include various buttons, dials, or other user interface and input components (e.g., touchscreens, touchpads, voice activated components) that enable a user to control the apparatus 100 during a procedure (e.g., decrease or increase illumination, take a photo or video, and so on).

FIG. 1B also includes a computing device 196 that communicates with the control device 190 (or the apparatus 100) over a network 192, such as the Internet. The computing device 195 provides various functions with the imaging needle apparatus, including the storing of images or videos captured by the apparatus, the display of the images and videos captured by the apparatus (e.g., in real-time during a procedure), the display of patient records or previously captured images/videos, and so on.

The techniques and systems introduced here can be implemented as special-purpose hardware (for example, circuitry), as programmable circuitry appropriately programmed with software and/or firmware, or as a combination of special-purpose and programmable circuitry. Hence, implementations can include a machine-readable medium having stored thereon instructions which can be used to program a computer (or other electronic devices) to perform a process. The machine-readable medium can include, but is not limited to, floppy diskettes, optical discs, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other types of media/machine-readable medium suitable for storing electronic instructions.

Figure 2:
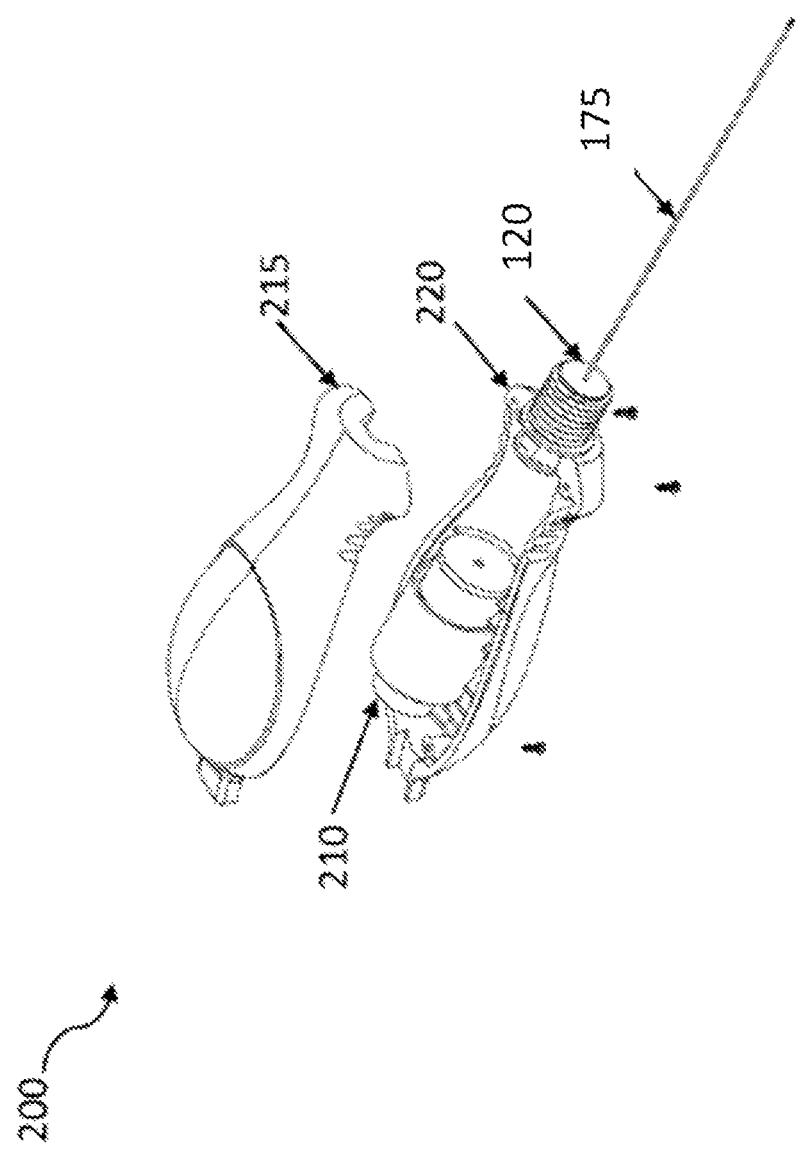
FIG. 2 is a diagram illustrating an imaging needle apparatus and integrated light engine.

As described herein, the imaging needle apparatus includes a light engine configured to provide a source of illumination capable of providing sufficient intensity within a small gauge (e.g., 18 G) needle during arthroscopic procedures. FIG. 2 is a diagram illustrating an imaging needle apparatus 200 with an integrated or internal light engine.

The imaging needle apparatus 200 includes a light engine 210 disposed between a top part 215 and bottom part 220 of the handpiece (depicted as opened to show the internal light engine 210). The handpiece is connected via an adapter 120, which also connects a camera cannula (or a needle) 175 to the assembly. As used herein, the term "needle" refers to an object having a slender shape that may or may not have a sharp or pointed tip.

In an embodiment, the light engine 210, or light engine assembly, includes one or more LEDs and one or more lenses, which operate to focus light emitted by the LEDs to a light tube or fiber that extends from the light engine (or proximate to the light engine) to a distal tip of the camera cannula 175, where one or more imagers (e.g., an imager assembly) are disposed. In other embodiments, the light engine assembly may use light sources other than LEDs, e.g., OLEDs, metal halide, or halogen.

For example, a video lens may be located, positioned, or disposed on a tip of the imaging needle apparatus 200. The imaging needle apparatus may therefore be suitable for recording forward-viewing imaging and/or video recording through the video lens, relying on light provided by the light engine 210. The lens may be extendable when, for example, fins are twisted or turned. The fins may be twisted along a direction circumferential to the needle (around a circumference of the needle). The lens may be locked in place, and a cutting edge of the needle (e.g., the outer cannula) may be covered when the video lens is extended out of the needle.

In some cases, the video lens allows users to easily navigate the tip of the needle into human joints and other spaces or body cavities. When the video lens is inside a joint or space, the probe may be extended, and the tip of the needle may be actively covered or uncovered during a procedure using the camera cannula 175 and associated video lens (e.g., see FIGS. 5A and 5B). Further, the tip of the probe may be coated so that it can be easily located using ultrasound. The coating on the tip may also provide additional guidance during a procedure.

The imager assembly may include various image sensors, such as active-pixel sensors (APS), including CMOS sensors, bee-eye sensors, and so on. Further details regarding the light engine 210 and the imager assembly or image sensors are described herein.

Once in place, the imagine needle apparatus 100, 200 can be utilized for precise targeting of fluids into imaged spaces. A retractable probe in the apparatus 200 can include ports that deliver injections of stem cells, platelet-rich plasma (PRP), biological glues, or other materials with precision and accuracy, all imaged during the procedure.

The imaging needle apparatus 100, 200 can be operated or utilized in various ways. For example, a user can place the tip into a patient's joint using the extended needle, image or capture the joint using the imaging assembly, identify a meniscal tear or flap in the joint based on the imaged joint, and treat the meniscal tear or flap. The user can treat the meniscal tear or flap by gluing the tear or flap down, shave off at least a portion of the meniscal tear or flap, and/or inject stem cells/PRP through the needle into the joint, as the case dictates. The whole procedure can be easily recorded (e.g., by video) using the imaging assembly, for documentation or future reference. Alternatively, the imaging needle apparatus 100, 200 can be used to image spaces and cavities in order to guide, within another port, a second micro-needle or nano-tool that can cut or otherwise manipulate tissues, as needed.

Thus, the imaging needle apparatus 100, 200, in various embodiments, may be much smaller and even less invasive (e.g., more suited for minimally invasive procedures) than traditional instruments. For example, the small imager probe (e.g., the camera cannula 175) can be disposed inside of a relatively small needle (e.g., a needle of 21.5-18.0 gauge), as compared to traditional instruments.

In addition, embodiments of the imaging needle apparatus 100, 200 can be utilized with other applications besides orthopedics applications. For example, aspects can be readily adapted to a broad variety of scopes and catheters, and thus can have a wide application within the many fields in medicine. For example, the imaging needle apparatus 100, 200 can be used to further miniaturize cardiac catheters, which can allow safer intra-vascular navigation and placement. The imaging needle apparatus 100, 200 can also be used as, or may become, a much smaller laparoscope.

As another example, various aspects of the imagine needle apparatus 100, 200 can be used for needle guidance applications and tissue biopsies of all types. The imaging needle apparatus 100, 200 may be inserted into a tissue, and the user can recognize and confirm tissue changes via the video lens of the small camera cannula 175, illuminated by the light engine 210. Accordingly, the imaging needle apparatus 100, 200 can be used to accurately biopsy or sample tissue as needed.

Further, the imaging needle apparatus 100, 200, in some cases, can be used to perform percutaneous procedures. For example, the small size of the needle and associated forward viewing lens system can assist all manner of office-based diagnostics and procedures. Eventually, current open surgical procedures performed in a hospital setting may one day be easily and safely done without general anesthesia in an office procedure setting using embodiments of the imaging needle apparatus 100, 200. The imaging needle apparatus 100, 200, therefore, can make procedures more convenient for both patients and doctors, while significantly reducing patient risk and health costs, among other benefits.

As described herein, the imaging needle apparatus 100, 200 includes various removable modules and components that are configured to be added or removed during different procedures and medical applications. FIGS. 3A-3M illustrate the various components of the imaging needle apparatus 100, 200.

Figure 3A:
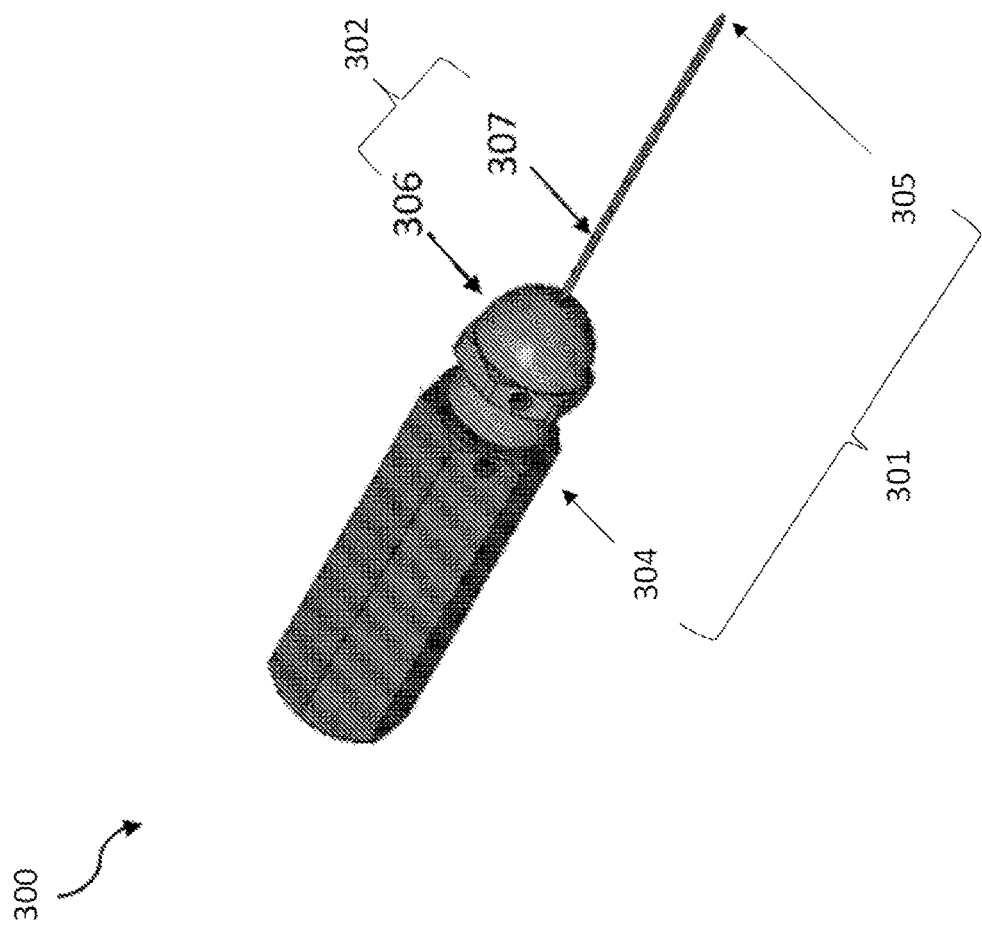
Figure 3B:
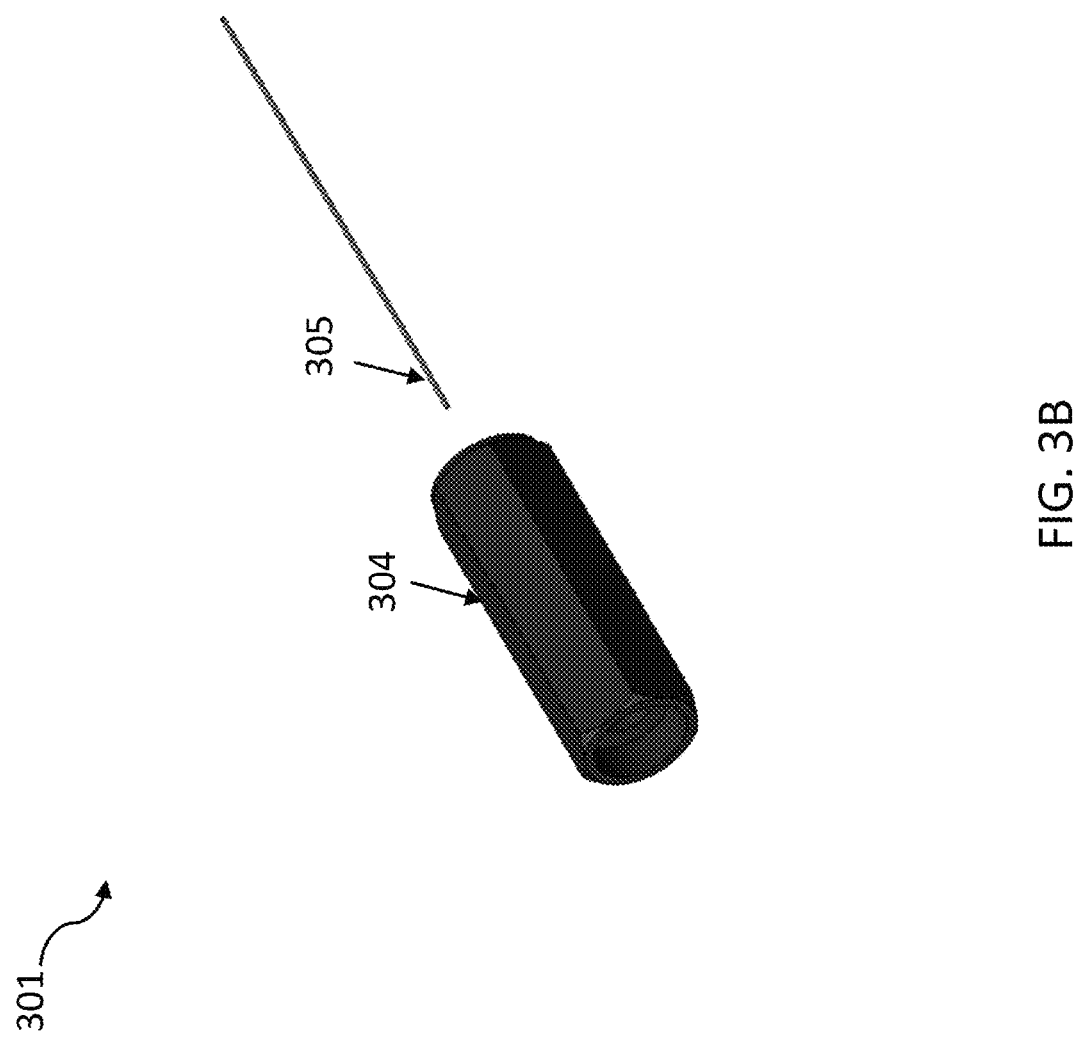

FIGS. 3A-3B depict an assembly 300 including a trocar assembly 301 and a cannula assembly 302 where the former is inserted into the latter. The trocar assembly 301 includes a handpiece 304 and a stylet 305. The cannula assembly 302 includes a hub 306 and a cannula 307 (e.g., a blunt cannula). FIG. 3A illustrates the stylet 305 inserted into the cannula 307, so only a tip of the stylet 305 is shown. In an embodiment, the cannula 307 has an inner diameter slightly larger than the stylet 305 or any needle (e.g., as the camera cannula 175) that may be inserted into the cannula 307 in order to prevent blood or other material from entering the trocar assembly 301 or the cannula assembly 302. FIG. 3B illustrates the stylet 305 of the trocar assembly 301.

Figure 3C:
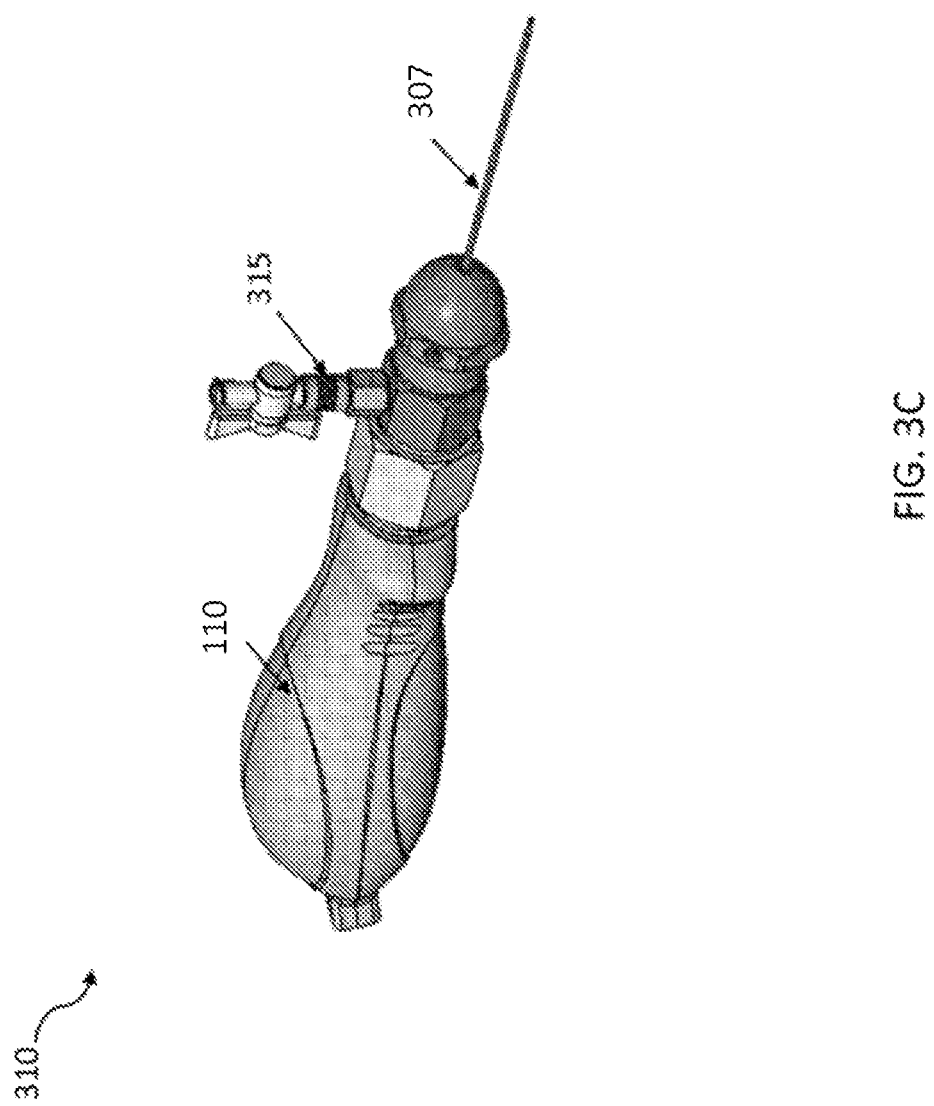

FIG. 3C depicts a nano-arthroscope assembly 310. The nano-arthroscope assembly 310 includes a handle or handpiece 110, a blunt cannula 307, and various hex adjusters 315, which connect the cannula 307 to the handpiece 110.

Figure 3D:
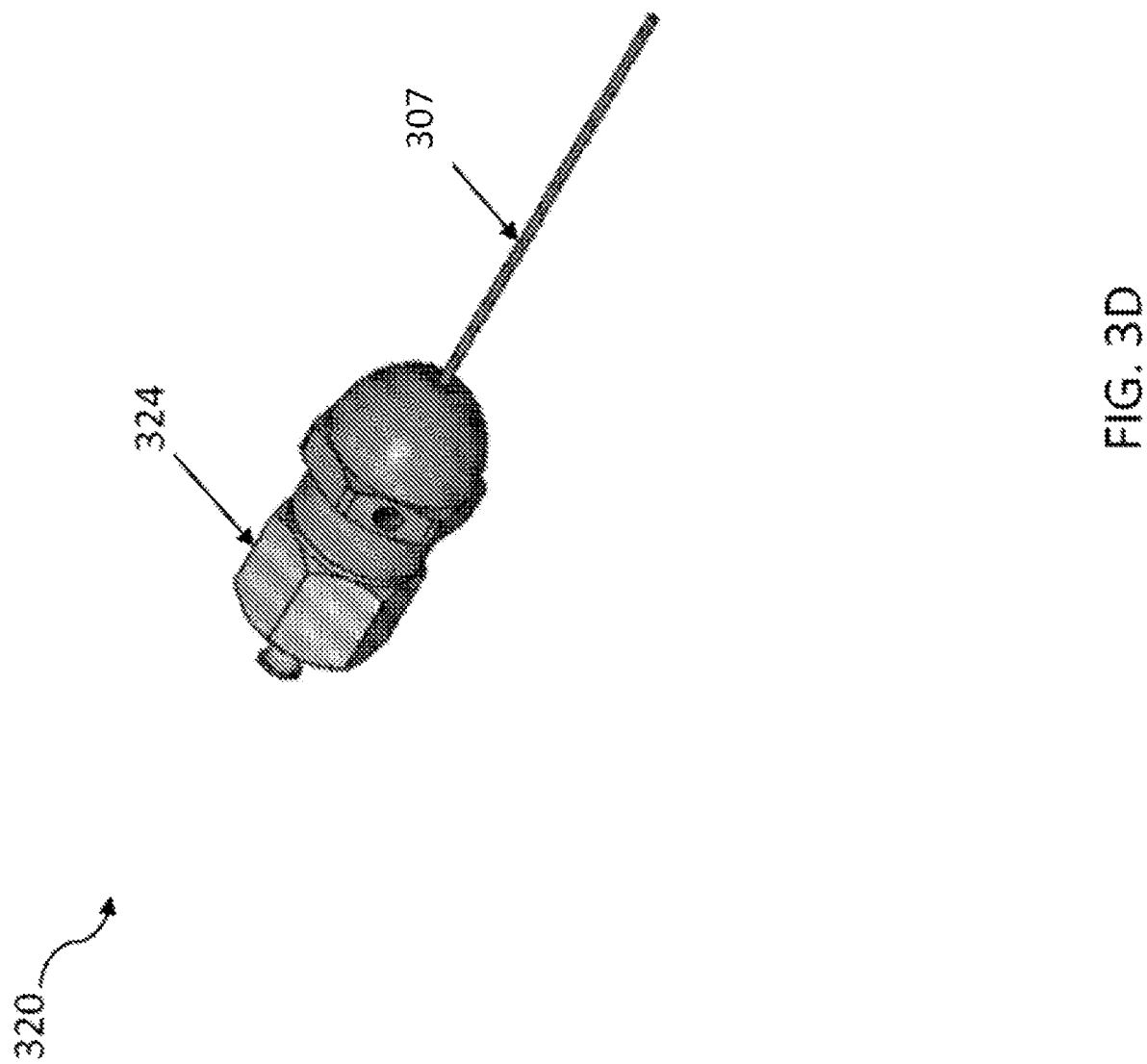

FIG. 3D depicts a syringe adapter assembly 320. The assembly 320 includes an adapter 324 that is configured to connect a syringe to a blunt cannula 307, such as the blunt cannula 307 of FIG. 3C.

Figure 3E:
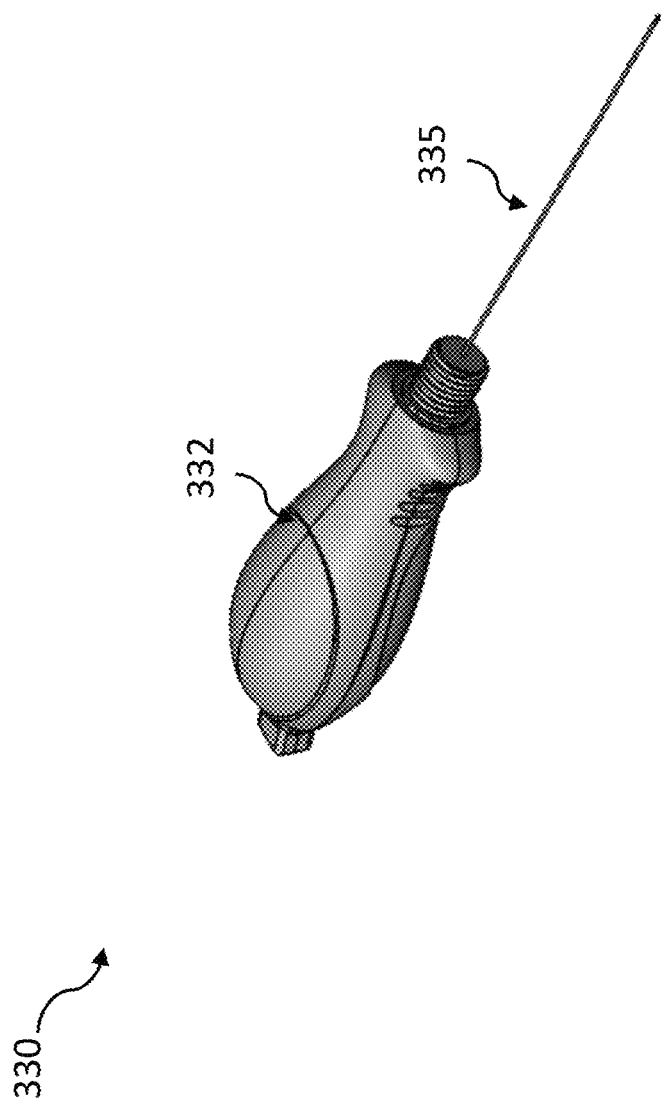

FIG. 3E depicts a nano-arthroscope assembly 330. The assembly 330 includes a handpiece 332 and camera cannula 335, which receives light from an internal light engine (not shown), such as light engine 210.

FIG. 3F depicts a hex adjuster assembly 350. The assembly 350 includes a proximal hex adjuster 140 connected to a distal hex adjuster 150.

FIG. 3G depicts an adapter 355 for the handpiece of the nano-arthroscope assembly, such as assembly 310.

Figure 3J:
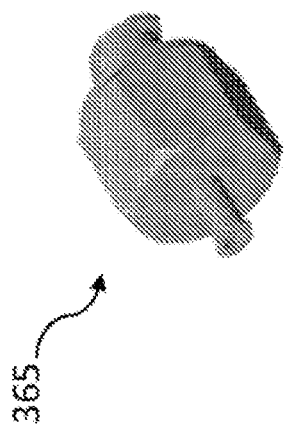
Figure 3I:
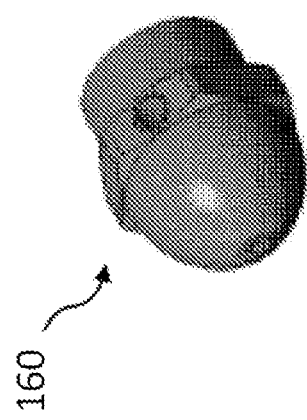
Figure 3H:
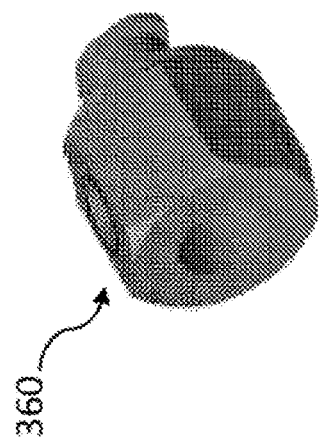

FIGS. 3H, 3I, and 3J depict a distal hex adjuster 360, a cannula adapter (or hub) 160, and a syringe adapter 365, respectively. Using the adapters and adjusters, as described herein, the imaging needle apparatus 100, 200 can enable a user to quickly add or remove components during a procedure. For example, the mating of an adapter to an adjuster enables the user to perform a quick-turn connect or disconnect action, in order to add or remove a component (e.g., a scope or syringe) while a portion of the apparatus 100 is being used on a patient.

Figure 3K:
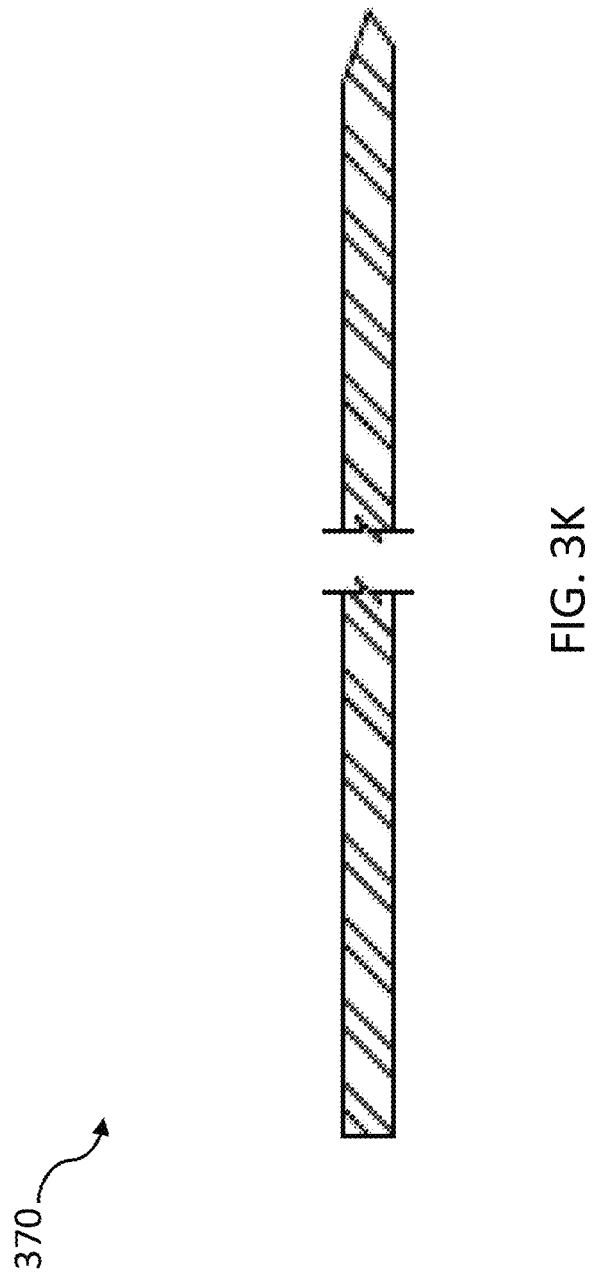
Figure 3L:

FIG. 3K depicts a stylet tip of the apparatus 100, and FIG. 3L depicts an outer cannula 380 of the apparatus 100. FIG. 3M depicts a camera cannula 175 of the apparatus 100. As described herein, the camera cannula 175 can include a body 392 and a distal end or tip 395, where one or more (e.g., four) image sensors (e.g., CMOS sensors) are disposed on an outer surface of the tip 395.

As described herein, the imaging needle apparatus 100 is a modular apparatus, where different components can be added or removed when in use during a medical procedure. The imaging needle apparatus 100 can have a body attached to a needle with a retractable tip. For example, the imaging needle may include a needle as well as a probe. The needle may be sufficiently sharp enough to pierce soft tissue, and the probe may be used to image the surrounding environment (e.g., a body cavity).

Either the needle or the probe may be retractable. When the probe extends beyond the sharp tip of the needle, the imaging needle apparatus 100 may be blunt. When the sharp tip of the needle extends beyond the blunt tip of the probe, the imaging needle apparatus may be sharp. The tolerances between the needle and the probe are such that a minimal amount of spacing is present to ensure unimpeded protraction and retraction of the probe with respect to the needle. Such tight tolerances allow shielding of the outer sharp cutting edge when the probe is protracted.

The retraction operation can be performed via a control mechanism. The probe can be retracted and housed inside of the needle when the control mechanism is in a first state and may be extended from the sharp tip of the needle when the control mechanism is in a second state. The control mechanism may be disposed on the body, such as on the housing or handpiece.

The control mechanism can include, for example, fins that extend radially from the body. The control mechanism can be, for example, a hub including two fins that extend on opposite sides of the body. A user can perform the retraction by rotating the fins. For example, a plate or tab attached to the probe can rotate through a spiral track along an interior surface of the hub as the fins are rotated around a rotation axis that is parallel to the needle.

The fins can also be accompanied by an indicator that shows whether the imaging needle is in a retracted state. The indicator can display a color that is based on whether the imaging needle is retracted. Accordingly, the indicator can inform the user of whether the blunt tip of the probe extends beyond sharp tip of the needle when the retractable tip is not visible to the user.

In some cases, the imaging needle can be used solely as an imaging device or may be used as an imaging device and as a mechanism to deliver fluid into a desired or target space. Fluid can flow through the needle according to pressure applied by the body of the imaging needle. The fluid through the side ports can be used to clear the viewing field of debris or tissue. During viewing, fluid flow can occur through the lumen and the side ports by operating a pressure source coupled to the imaging needle, as described herein.

The pressure source can exert pressure on the fluid using, for example, a syringe, a bulb, a pump, and/or a similar structure, which is coupled to a fitting disposed on the body of the imaging needle.

An imager (e.g., image sensor and associated components) in the probe can be used to image the surrounding environment through a transparent cover on the distal end of the probe. A distal end of the probe is the farthest end of the probe from the body of the imaging needle apparatus. The imager can be disposed distal to the holes in the sides of the probe.

The diameter of the needle may be relatively small (e.g., ~18 G), because the imager can be relatively small. The imager can include one or more cables, a stack of ICs, an imager chip, one or more light pipes, and a lens. The imager can have a bee-eye imager configuration. The imager can include an IC stack having multiple photocells and a lens assembly. The lens assembly can include a Fresnel lens.

The one or more cables can transmit electrical signals between the imager and an external device (e.g., computing device 195), such as a device including a memory and one or more processors, a device including a display, a device providing a voltage source, or various combinations.

The stack of ICs and the imager can convert light signals into the usable electrical signals transferred through the one or more cables. The imager can correspond to a plurality of pixels. For example, the resolution of the imager corresponds to the number of photocells and/or pixels in the imager.

The one or more light pipes can guide light to and from the cover of the probe. The light pipes can include illumination light pipes, which may transmit light through the cover in order to illuminate an area that is being imaged. The illumination light pipes can be disposed along the interior of the probe. The illumination light pipes can extend along an outer edge of the imager chip and the IC stack and can be bundled with the one or more cables. The illumination light pipes can guide light from one or more LEDs.

The one or more light pipes can also include a focusing light pipe. The focusing light pipe can be disposed between the imager chip and the lens of the imager. The focusing light pipe can transmit focused light from the lens to the imager. The illumination light pipes can be disposed around an outer circumference of the focusing light pipe. The lens can be disposed between the imager and the cover of the imaging needle apparatus. The lens can focus light onto the imager.

The cover can be disposed over the probe. The cover can be transparent, such that light from the illumination light pipes may be transmitted through the cover.

In some cases, fluid can also flow through a lumen within the probe, and through side ports at the tip of the probe. The side ports can be disposed in the cover of the probe and can be between illumination light pipes in the probe. When the probe is retracted inside of the needle, for example, the side holes are covered, and the fluid flows out of the needle at a relatively low flow rate. When the probe is extended, the side holes are exposed, and the fluid can freely flow out of the side holes.

In order to connect the circuitry within the apparatus to external devices, such as voltage sources and computers for image analysis, the cables can extend directly to circuits within the apparatus. However, when the apparatus includes relatively small imagers, the apparatus may be difficult to manufacture using the cables alone. Furthermore, the cables can become dislodged from the circuitry in the apparatus when fluid flows through the apparatus.

According to various embodiments, an interposer is connected between the cables and the internal circuitry of the imaging needle. For example, the interposer is coupled between the cables and a plurality of light sources and/or the imager. The interposer includes relatively small lines and electrical contacts disposed in a semiconductor or insulative substrate. The lines and contacts are generated using photolithography. The interposer is relatively easy to manufacture and can take up less space within the imaging needle apparatus than the cables. In addition, the interposer can be easier to install between the bundle of cables and the internal circuitry of the imager needle. Thus, in some embodiments, the imaging needle apparatus 100 includes components configured to illuminate target areas of a patient through a small (e.g., 18 G) needle or cannula.

Figure 4A:
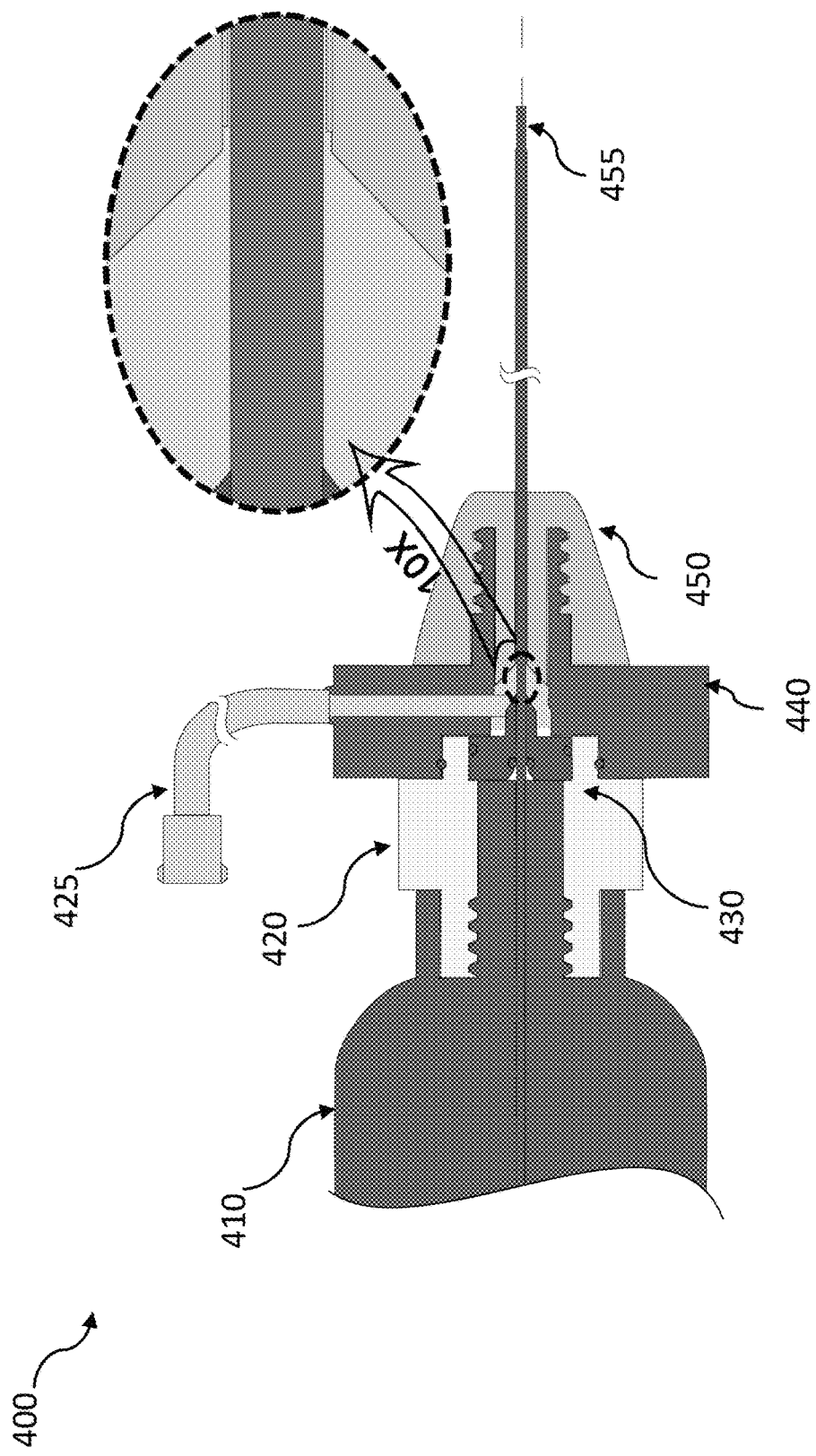
FIGS. 4A-4B are diagrams illustrating an example endoscope.
Figure 4B:
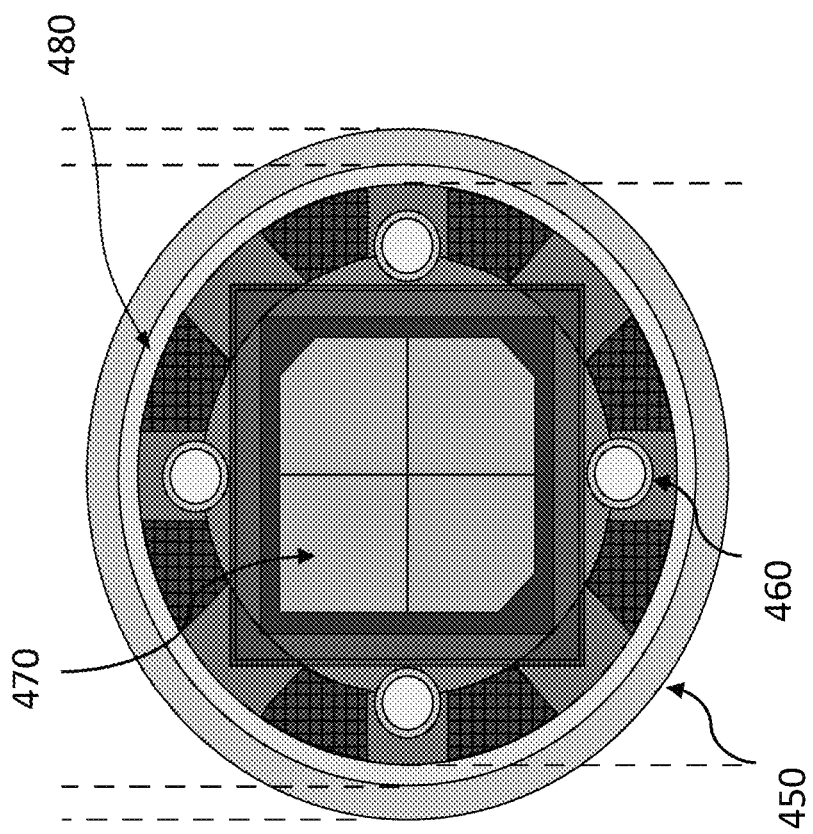

FIGS. 4A-4B are diagrams illustrating an example endoscope, as described herein. Referring to FIG. 4A, the endoscope 400 is a 19-gauge endoscope having a probe extend from an 18-gauge outer cannula. The endoscope 400 includes a handpiece 410 (which stores LEDs and modifying or focusing optics, as described herein) that is coupled to an inner hex ring 420.

The inner hex ring 420 is positioned via an O-ring holder 430, which holds O-rings. A scope adapter 120 receives the holder 430 and an outer blunt cannula 450. A probe (e.g., camera cannula) 455, extends outwards from the outer blunt cannula 450. Further, a one-way luer 425, which facilitates the injection of fluids (e.g., from an attached syringe), connects to the scope adapter 120. As depicted in the enlarged section, the endoscope 400 enables the flow of fluids through the outer blunt cannula 450 while the probe 455 is positioned within the cannula 450.

FIG. 4B depicts a distal end view of the endoscope 400. Within the outer cannula 450 is the probe, which includes four light pipes or light fibers 460 disposed around a camera 470 or image sensor. Further, fluid injection lumen 480 is also within the outer cannula 450. Thus, during a procedure, light from the light pipes 460 illuminates a target area of a patient (e.g., a knee joint), which can be imaged by the camera 470 and or treated using the injected lumen 480.

As described herein, the imaging needle apparatus 100 can include a double hex nut scope adapter that allows tightening of a scope handpiece without spinning the scope and tightening of the outer cannula without spinning the cannula. Further, each luer (e.g., luer 425) can be connected with an on-off valve that leads to a channel between the outer cannula and the camera cannula. Thus, the channel between the outer cannula and the camera cannula can have zero-degree outflow, allowing precision injection under direct visual control.

Figure 5A:
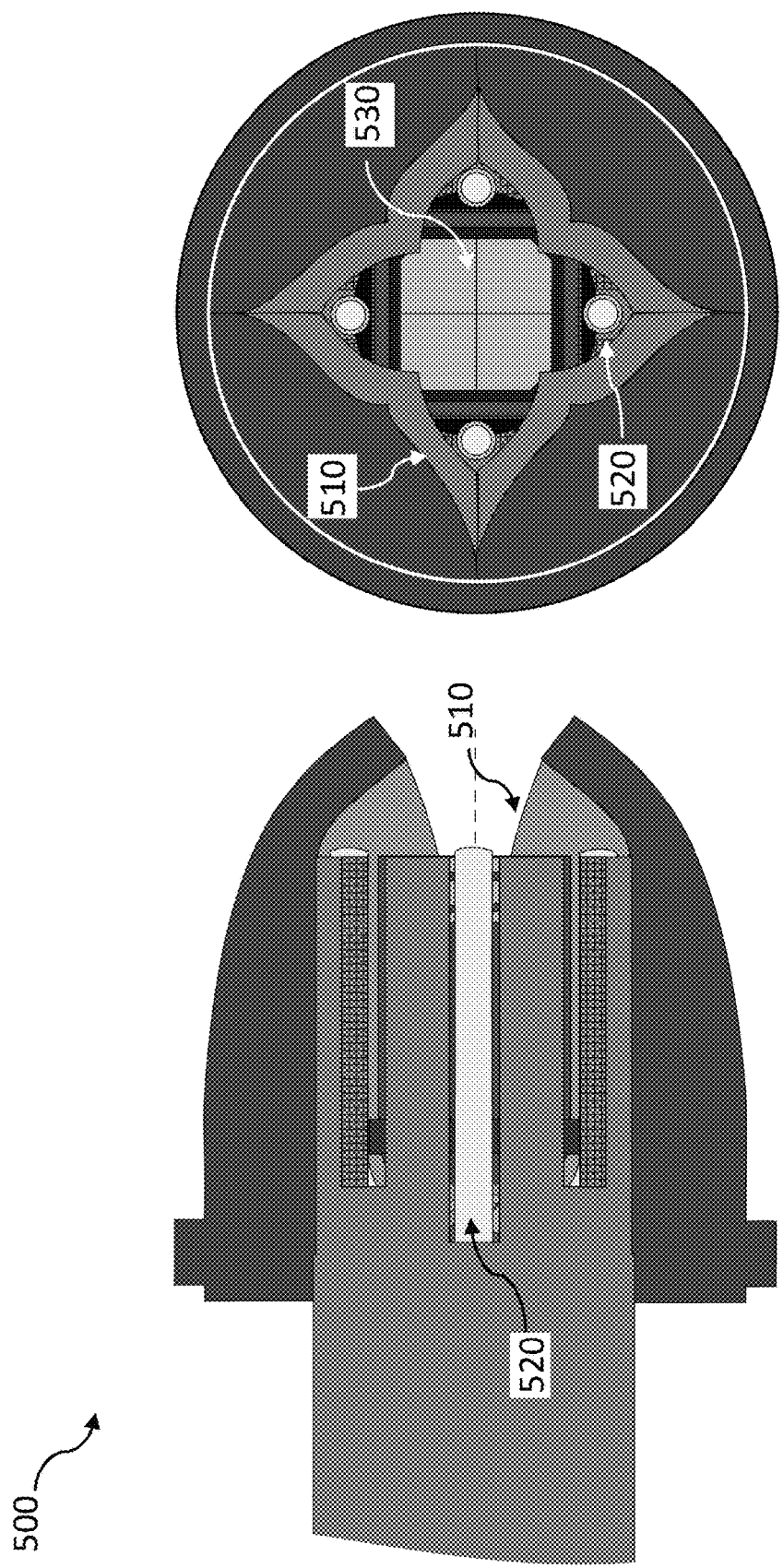
FIGS. 5A-5B are diagrams illustrating the use of a camera cannula and internal flap valve.
Figure 5B:
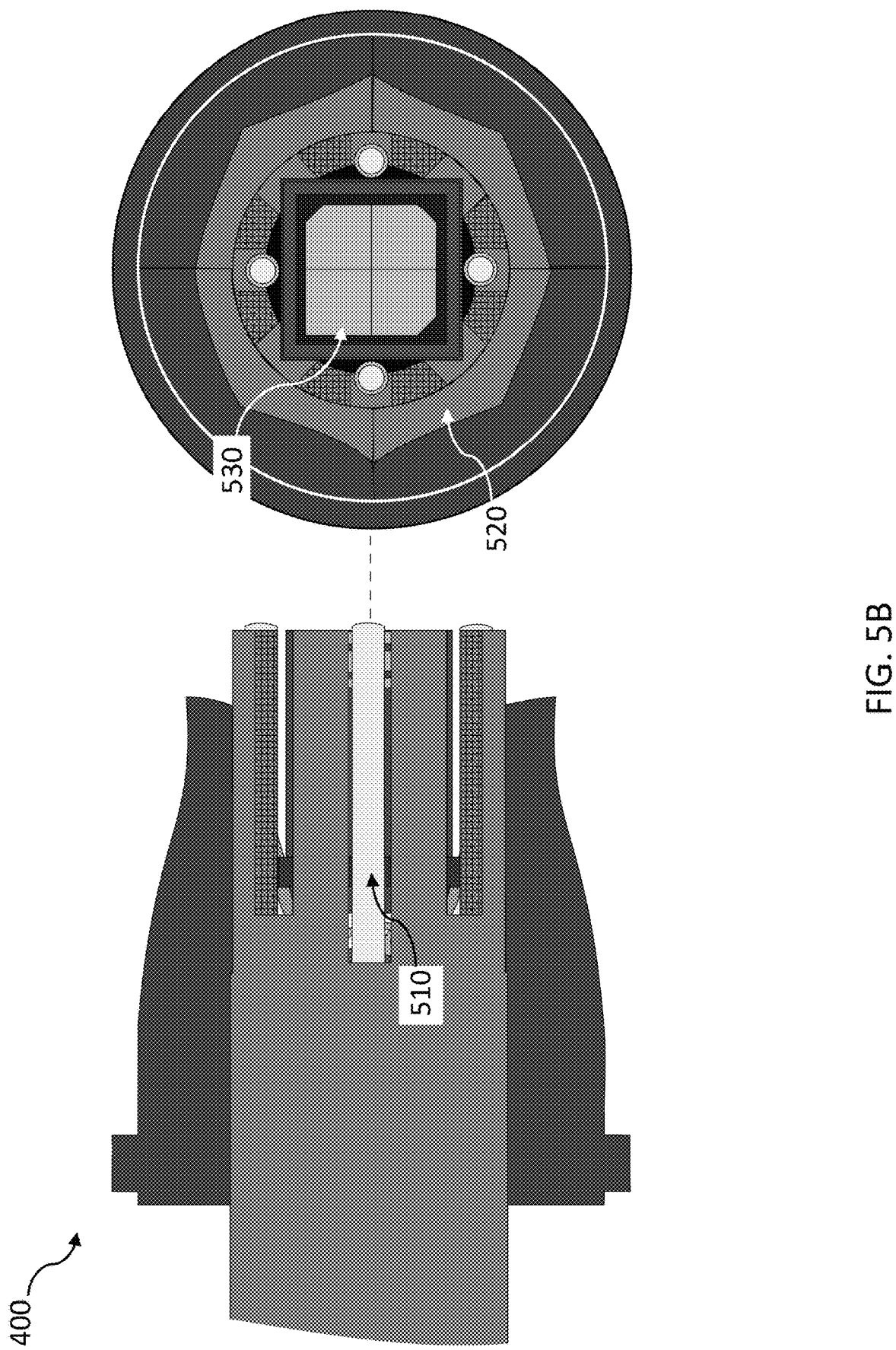

The apparatus 100 can also include a central port or adapter for the camera cannula that has a flap valve, which allows for the use or removal of a camera cannula while maintaining the pressure in a target joint and within the apparatus 100. FIGS. 5A-5B are diagrams illustrating the use of a camera cannula and internal flap valve 500.

In some cases, the flap valve 500 on a central camera cannula port can allow introduction of additional ports in a knee joint, as well as moving the scope between ports without losing pressure in the apparatus. For example, different ports can be utilized for a same joint, or at different joints or areas of a body, all during the same procedural session or treatment.

When a camera cannula, having light pipes 520 and a camera 530, extends through the valve, flaps 510 of the valve open to receive the cannula. However, when the camera cannula is removed, the flaps 510, preventing any loss of pressure when using the camera cannula. Thus, a user can remove the camera cannula and handpiece from one port and put the cannula in another port. For example, the original port can be used for a 19 G bone needle to bore a hole through the cartilage under direct visualization. Thus, all actions can be performed while maintaining positive pressure in the joint via fluid insufflation.

As described herein, the apparatus 100 enables interchangeable cannulae. The standard 18 G blunt cannula can be replaced with other cannulae. For example, the 17 G blunt cannula can be used if a user should desire to inject a more viscous solution under direct visualization. The blunt cannulae can be introduced with an inner stylet, facilitating smooth entry into joints with minimal collateral damage to tissues. Optionally, a beveled outer cannulae can be provided if physicians desire the option of direct entry into spaces without a stylet (e.g., trocar assembly).

Figure 6:
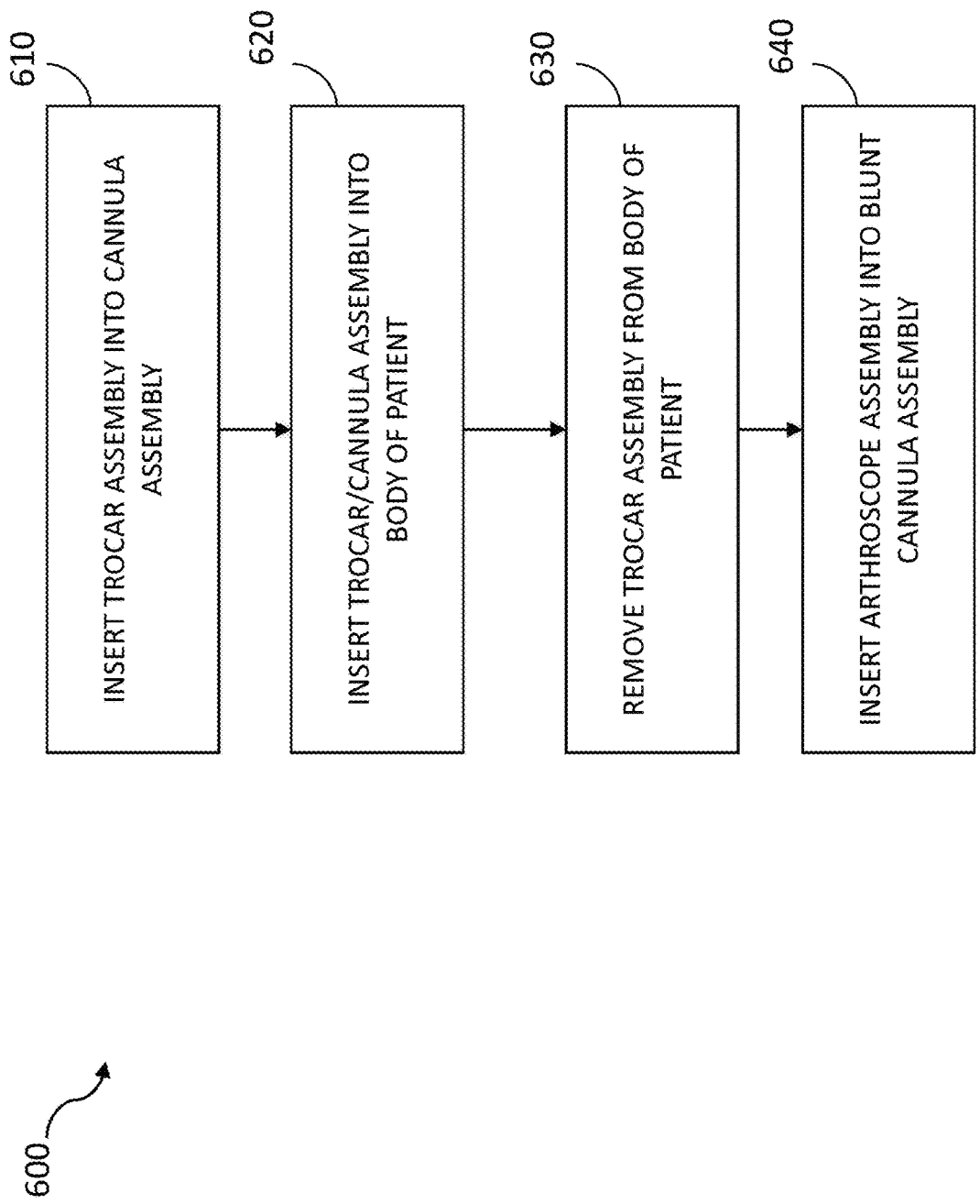
FIG. 6 is a flow diagram illustrating a method of treating a patient with the imaging needle apparatus.

Thus, the imaging needle apparatus 100, being configured as a set of removable modules, facilitates the interchange of components when treating a patient. FIG. 6 is a flow diagram illustrating a method 600 of treating a patient with the imaging needle apparatus.

In step 610, a doctor (or user) inserts the trocar assembly into the cannula assembly. In step 620, the doctor inserts the resulting assembly of the trocar assembly and the/cannula assembly into the patient's body. In step 630, the doctor removes the trocar assembly from the cannula assembly. In step 640, the doctor inserts the arthroscope assembly (e.g., including the camera cannula) into the blunt cannula assembly.

Once inserted, the camera cannula can be extended outwards from the blunt cannula assembly, in order to provide a larger viewing angle within the target area of the patient, such as a joint cavity. Further, the doctor can attach a syringe and, via the blunt cannula assembly, provide fluids or other material to the target area while also viewing the target area during the procedure.

In some cases, the doctor can remove the arthroscope assembly while maintaining the blunt cannula assembly in the port of the patient and utilize one or more tools to treat the patient (e.g., glue a tear or shave a small section of bone) via the blunt cannula assembly. The doctor can utilize a second port near the first port and insert the arthroscope assembly via the second port (and via another cannula assembly), in order to view and image the treatment procedure.

Examples of the Light Engine

As described herein, the imaging needle apparatus 100 includes a light engine configured to provide a sufficient amount of illumination through a needle or cannula during a medical procedure using optics adapted to fit within a handpiece or housing of an arthroscope assembly. In an embodiment, the light engine is configured to provide sufficient illumination through an 18-gauge needle or 19-gauge needle.

In some embodiments, the light engine assembly, or light engine, includes a light source (e.g., a mounted LED), a lens or prism to focus the light, and one or more light tubes or fibers. The light engine assembly amplifies the light that is transmitted into small diameter light tubes within a 19 G or 18 G inner camera cannula. In an embodiment, the light source and the lens or prism are provided in the handpiece (e.g., 110) of the imaging needle apparatus. In another embodiment, the lens or prism is provided in the handpiece while the light source is provided external to the handpiece.

For example, the light engine includes a LED light source with current regulation and adjustment to provide a variable intensity light source. The light source has its light output characteristics modified through use of an LED collimating optic attached to the LED light source to produce an increase in light intensity and collimated light, especially in the center of the modified light beam. The center portion of the light beam exiting the collimated optic then passes through an aperture, which allows only collimated light from the center of the beam to pass.

The collimated light that has passed through the aperture moves into a visible light ball lens, which creates a focal point where the light intensity is greatly increased. The light exits the ball lens, and four fiber optic strands, tubes, pipes, or fibers are positioned such that the open ends of the fibers are adjusted and held at or near (e.g., slightly behind) the focal point of the ball lens. Positioned at or near the focal point of the light exiting the ball lens, the light fibers each receive high intensity light coupled into the ends of the fibers. The light travels through the light fibers, exiting at the other end of the canula (e.g., the tip), providing light so an associated imaging device, also disposed at the tip of the cannula, can collect photons and capture images of target body areas.

Figure 7:
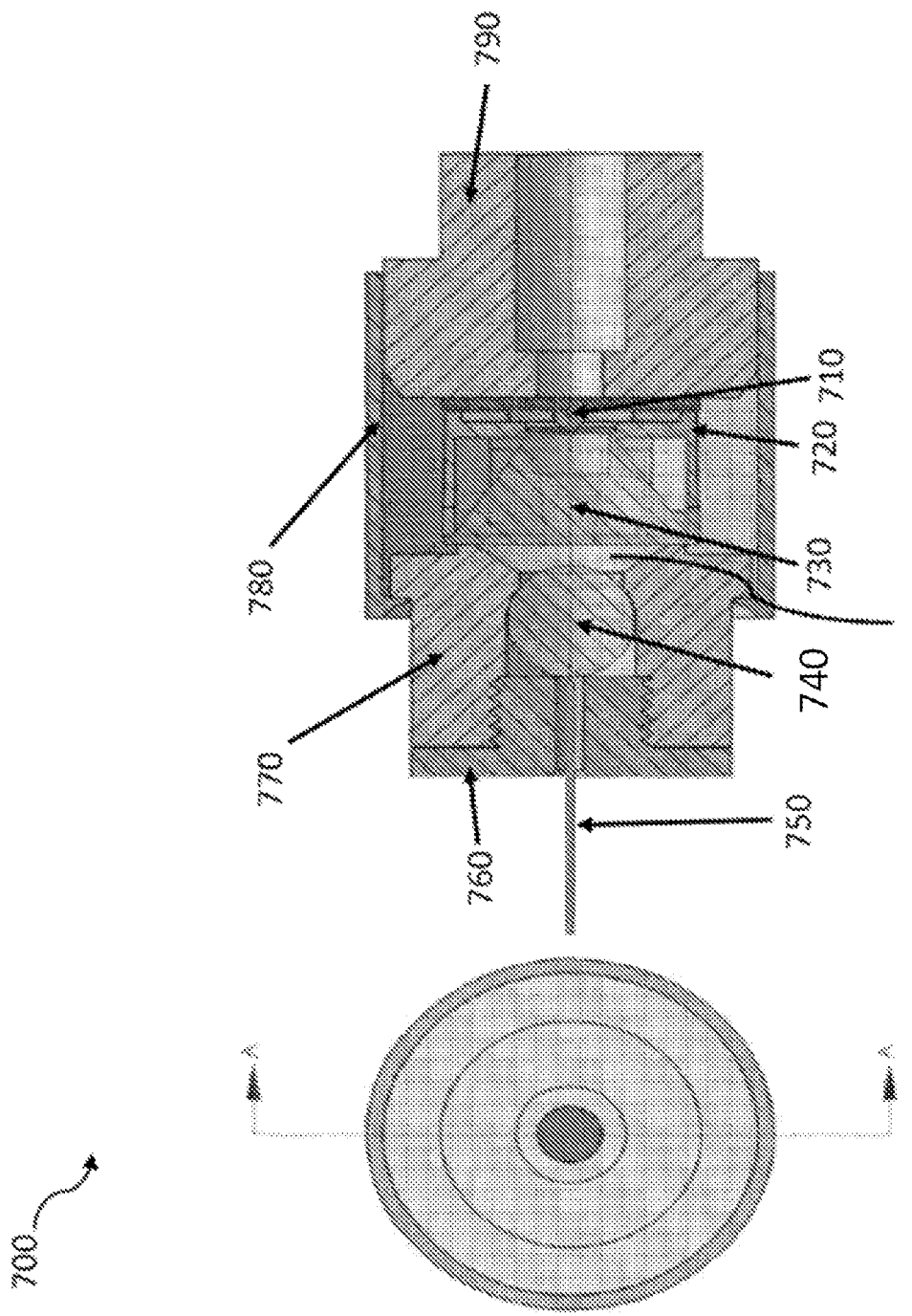
FIG. 7 is a diagram illustrating components of a light engine configured to provide illumination for the imaging needle apparatus.

FIG. 7 is a diagram illustrating components of a light engine 700 configured to provide illumination for the imaging needle apparatus 100. As described herein, the light engine generates a beam of light capable of providing high intensity illumination within an 18-gauge or higher cannula or needle.

The light engine 700 includes a solid-state LED light source 710. The LED light source 710 includes an LED mounted on an aluminum circuit board. The light source 710, in collaboration with a control device (e.g., control device 190) includes current regulation and adjustment to provide a variable intensity light source that can be modified (e.g., increased or decreased) during a procedure.

The light source 710 has its light output characteristics modified through use of an LED collimating optic 730 attached to the LED light source 710 via an optic holder 720. The collimating optic 730 produces an increase in light intensity and collimates the light received from the LED, especially at a center portion of the modified light beam. In some embodiments, the collimating optic 730 is a TIR (total internal reflection) type collimating optic, such as a TIR collimator or TIR lens.

The center portion of the light beam exiting the collimated optic 730 then passes through an aperture 745 which primarily allows the collimated light from the center of the beam to pass through. The collimated light passing through the aperture 745 is then introduced into a visible light ball lens 740. The ball lens 740 creates a focal point of the light where the light intensity is greatly increased. In some cases, the ball lens is formed from a single substrate of glass and can focus or collimate light, depending upon the geometry of the input source. In some cases, half-ball lenses can be used, depending on the design and configuration of the light engine 700.

Four fiber optic strands or fibers 750 are positioned such that the open ends of the fibers 750 are adjusted and held at or near the focal point of the ball lens 740, allowing high intensity light to be coupled into the ends of the fibers 750. The fibers 750 are disposed as a bundle and positioned via at or slightly past the focal point of the light exiting the ball lens 740. For example, in some embodiments, a bundle of one or two fibers may be positioned at the focal point, whereas a bundle of three, four, or more fibers may be positioned slightly past (distal from) the focal point of light exiting the ball lens 740.

The other end of the fibers 750 surround a camera or image sensor at a tip of a camera cannula. At this end, the high intensity light exits the fibers 750, providing light sufficient for the image sensor to capture images of target areas.

To maintain the configuration of the optics of the light engine 700, a ball lens retainer 770 and ball lens holder 760 is disposed within the light engine 700. Further, the light engine 700 includes a housing (e.g., aluminum) 780 and thermal slug 790, which protects the light engine 700 and other components that contain the light engine 700, such as the nano-arthroscope assembly described herein.

Thus, as described herein, the imaging needle apparatus 100 can include the light engine 700. For example, the light engine 700 can be placed in a handle or handpiece 110 of the imaging needle apparatus 100. Thus, the configuration of the light engine 700 is based on providing sufficient intensity of illumination for the imaging needle apparatus 100, such as an assembly having 18-gauge cannulae.

Figure 8:
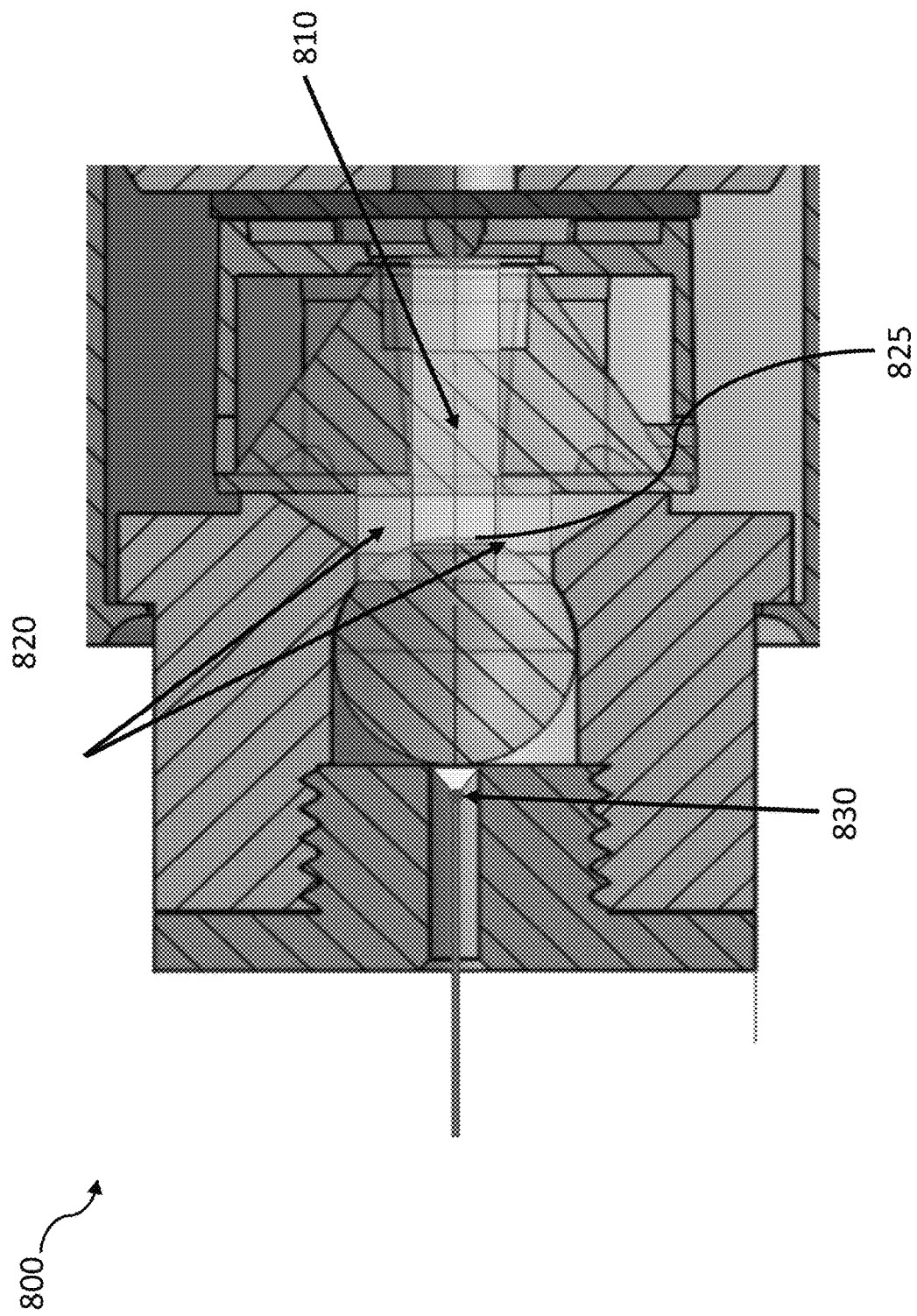
FIG. 8 is a diagram illustrating the modification of light within the light engine.

FIG. 8 is a diagram 800 illustrating the modification of light within the light engine 700. As depicted, an LED light source emits light 810. A collimating optic (e.g., a TIR lens) collimates and increases the intensity of the light 820. The collimated light passes through an aperture 825, which allows a center portion of the light (e.g., a collimated, high intensity portion) to pass into a ball lens. The ball lens focuses the light to a focal point 830, where there is an increased intensity of the collimated light. A bundle of light fibers is positioned at the focal point of the ball lens. The light at the focal point is coupled into the light fibers, and travels to the other end of the fibers, which is at the tip of a camera cannula.

The light exits the fibers and illuminates a body cavity or other target area, which can then be imaged by an image sensor or camera also positioned at the tip of the cannula.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of implementations of the system is not intended to be exhaustive or to limit the system to the precise form disclosed above. While specific implementations of, and examples for, the system are described above for illustrative purposes, various equivalent modifications are possible within the scope of the system, as those skilled in the relevant art will recognize. Also, while processes or blocks are at times shown as being performed in series, these processes or blocks may instead be performed in parallel or may be performed at different times. Further, any specific numbers noted herein are only examples: alternative implementations may employ differing values or ranges.

The teachings of the methods and system provided herein can be applied to other systems, not necessarily the system described above. The elements, blocks and acts of the various implementations described above can be combined to provide further implementations.

Any patents, applications and other references noted above, including any that may be listed in accompanying filing papers, are incorporated herein by reference. Aspects of the technology can be modified, if necessary, to employ the systems, functions, and concepts of the various references described above to provide yet further implementations of the technology.

Light Engine (Embodiments in Claim Format):

A1. A light engine for a nano-arthroscope assembly, the light engine comprising:
  a light source, wherein the light source includes a light emitting diode (LED) mounted to a circuit board;
  a collimating optic positioned proximate to the LED, wherein the collimating optic collimates light emitted from the LED and increases an intensity of the light emitted from the LED;
  a ball lens positioned to receive the light collimated by the collimating optic, wherein the ball lens focuses the received light to a focal point outside of the ball lens; and
  a bundle of light fibers positioned proximate to the ball lens, wherein the bundle of light fibers includes a first end that is positioned at the focal point of the light focused by the ball lens such that the light is coupled into the first end of the bundle of light fibers at the focal point.

A2. The light engine of claim A1, further comprising:
  an aperture positioned between the collimating optic and the ball lens, wherein the aperture allows a center portion of the collimated light to pass from the collimating optic to the ball lens, and wherein the light engine is disposed within a handpiece of the nano-arthroscope assembly.

A3. The light engine of claim A1, wherein the collimating optic is a total internal reflection (TIR) collimator.

A4. The light engine of claim A1, wherein the bundle of light fibers is disposed on a camera cannula of the nano-arthroscope assembly that includes an image sensor configured to capture images illuminated by the light passing through the bundle of light fibers.

A5. The light engine of claim A1, wherein the bundle of light fibers is disposed on a camera cannula that is located within and extendable out of an 18-gauge cannula of the nano-arthroscope assembly.

A6. The light engine of claim A1, wherein the light source is electrically coupled to a control device configured to vary the intensity of the light emitted by the LED.

A7. The light engine of claim A1, wherein the bundle of fibers includes four light fibers disposed around an image sensor of a camera cannula of the nano-arthroscope assembly.

A8. The light engine of claim A1, wherein the bundle of fibers includes two or more light fibers disposed around an image sensor of a camera cannula of the nano-arthroscope assembly.

A9. The light engine of claim A1, wherein the nano-arthroscope assembly is configured to be disposed within an 18-gauge cannula during treatment of a patient.

A10. A method performed by a light engine of an nano-arthroscope for providing illumination during an arthroscopic procedure using the nano-arthroscope, the method comprising:
collimating light emitted from a light source of the light engine;
focusing the collimated light to a focal point;
coupling the focused light into a bundle of light fibers at the focal point; and
passing the coupled light through the bundle of light fibers to a body cavity within which the nano-arthroscope is located.

A11. The method of claim A10, further comprising:
before focusing the collimated light to the focal point, separating a center portion of the collimated light from the collimated light.

A12. The method of claim A10, wherein focusing the collimated light to a focal point includes focusing only a center portion of the collimated light to the focal point.

A13. The method of claim A10, wherein a light emitting diode (LED) mounted to a circuit board of the light engine emits the light as the light source.

A14. The method of claim A10, wherein the light emitted from the light source has an intensity variable by a control device electrically coupled to the light engine.

A15. The method of claim 10, wherein the light emitted from the light source is collimated by a total internal reflection (TIR) collimator.

A16. The method of claim A10, wherein the collimated light is focused to the focal point by a ball lens.

A17. The method of claim A10, wherein the collimated light is focused to the focal point by a half-ball lens.

A18. The method of claim A10, wherein coupling the focused light into a bundle of light fibers at the focal point includes coupling the focused light into four light fibers surrounding an image sensor of a camera cannula of the nano-arthroscope.

A19. An imaging needle apparatus, comprising:
a nanoscope assembly; and
a light engine contained within the nanoscope assembly.

A20. The imaging needle apparatus of claim A19, wherein the light engine includes:
a light source, wherein the light source includes a light emitting diode (LED) mounted to a circuit board;
a collimating optic positioned proximate to the LED, wherein the collimating optic collimates light emitted from the LED and increases an intensity of the light emitted from the LED;
a ball lens positioned to receive the light collimated by the collimating optic, wherein the ball lens focuses the received light to a focal point outside of the ball lens where one or more light fibers are positioned to receive the focused light; and
an aperture positioned between the collimating optic and the ball lens, wherein the aperture allows a center portion of the collimated light to pass from the collimating optic to the ball lens.

These and other changes can be made to the invention in light of the above Detailed Description. While the above description describes certain implementations of the technology, and describes the best mode contemplated, no matter how detailed the above appears in text, the invention can be practiced in many ways. Details of the system may vary considerably in its implementation details, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the invention to the specific implementations disclosed in the specification, unless the above Detailed Description section explicitly defines such terms. Accordingly, the actual scope of the invention encompasses not only the disclosed implementations, but also all equivalent ways of practicing or implementing the invention under the claims.

What is claimed is:
1. An apparatus for performing arthroscope procedures, the apparatus comprising:
a blunt cannula assembly including a blunt cannula;
a nano-arthroscope assembly configured to be disposed within the blunt cannula assembly, wherein the nano-arthroscope assembly captures images of a cavity within a body of a patient when extended outwards from the blunt cannula into the cavity; and
an adapter configured to facilitate management of fluids through the blunt cannula assembly while the nano-arthroscope assembly is disposed within the blunt cannula assembly,
wherein the nano-arthroscope assembly includes a light engine located within a handpiece of the nano-arthroscope assembly, the light engine providing illumination for the nano-arthroscope assembly and including:
a light source, wherein the light source includes a light emitting diode (LED);
an optic positioned proximate to the LED, the optic collimating light emitted from the LED;
an aperture allowing a portion of the collimated light to pass therethrough; and
a lens positioned to receive the passed portion of the collimated light and focus the received light to a focal point outside of the lens where one or more light fibers are positioned to receive the focused light, and wherein the aperture is disposed between the optic and the lens.

2. The apparatus of claim 1, wherein the nano-arthroscope assembly includes a camera cannula disposed within the blunt cannula, the camera cannula including an image sensor and one or more light fibers that provide illumination for the image sensor.

3. The apparatus of claim 1, wherein the nano-arthroscope assembly includes a camera cannula disposed within the blunt cannula, the camera cannula including an image sensor and a plurality of light fibers disposed on sides of the image sensor that provide illumination for the image sensor, wherein the image sensor has a plurality of corners inserted into a plurality of first slots in a wall of the camera cannula, and the plurality of light fibers are disposed in a plurality of second slots in the wall of the camera cannula.

4. The apparatus of claim 1, wherein the light engine provides a variable intensity light for the nano-arthroscope assembly, and the aperture is positioned between the optic and the lens.

5. The apparatus of claim 1, wherein the nano-arthroscope assembly includes:
an imager configured to capture the images of the cavity within the body of the patient.

6. The apparatus of claim 1, further comprising:
a syringe adapter configured to connect a syringe such that fluids from the syringe flow through the blunt cannula assembly to the cavity within the body.

7. The apparatus of claim 1, wherein the blunt cannula assembly includes an 18-gauge cannula.

8. The apparatus of claim 1, wherein the nano-arthroscope assembly includes an adapter having a quick-turn attachment mechanism that facilitates an attachment of a different handpiece to the nano-arthroscope assembly while the nano-arthroscope assembly is disposed within the blunt cannula assembly.

9. The apparatus of claim 1, wherein the adapter includes a flap valve that opens when a camera cannula of the nano-arthroscope assembly is extended through the blunt cannula assembly into the cavity of the body.

10. The apparatus of claim 1, wherein the nano-arthroscope assembly includes:
a control device disposed within the handpiece and configured to control operation of one or more image sensors of the nano-arthroscope assembly or a light source of the nano-arthroscope assembly.

11. The apparatus of claim 1, wherein the nano-arthroscope assembly is electrically coupled to an external control device that controls operation of one or more image sensors of the nano-arthroscope assembly or a light source of the nano-arthroscope assembly.

12. The apparatus of claim 1, wherein the lens is a ball lens, and ends of the light fibers are positioned at the focal point of the ball lens.

13. The apparatus of claim 12, wherein end surfaces of the light fibers are positioned at the focal point of the ball lens.

14. The apparatus of claim 1, wherein the lens is partially inserted into the aperture.

15. The apparatus of claim 14, wherein the light engine further comprises:
an optic holder coupling the optical component to the light source;
a lens retainer within which the lens is disposed;
a lens holder coupled to the lens retainer and having a hole through which the bundle of fibers passes; and
a housing accommodating the lens retainer, the aperture, the optical component, the optic holder, and the light source.

16. The apparatus of claim 1, wherein the aperture has a first side positioned proximate to the optic and a second side poisoned proximate to the lens, a size of the second side being smaller than that of the first side to allow a center portion of the collimated light and block the remaining portion of the collimated light.

17. An imaging needle apparatus, comprising:
a blunt cannula assembly including a blunt cannula; and
a nano-arthroscope assembly,
wherein the nano-arthroscope assembly includes a light engine located within a handpiece of the nano-arthroscope assembly, the light engine providing illumination for the nano-arthroscope assembly and including:
a light source, wherein the light source includes a light emitting diode (LED);
an optic positioned proximate to the LED, the optic collimating light emitted from the LED;
an aperture allowing a portion of the collimated light to pass therethrough; and
a lens positioned to receive the passed portion of the collimated light and focus the received light to a focal point outside of the lens where one or more light fibers are positioned to receive the focused light, and
wherein the aperture is disposed between the optic and the lens.

18. The apparatus of claim 17, wherein the nano-arthroscope assembly includes:
a camera cannula configured to extend within the blunt cannula assembly and into a joint of a patient.

19. The apparatus of claim 18, wherein the camera cannula is disposed within the blunt cannula, the camera cannula including an image sensor and a plurality of light fibers disposed on sides of the image sensor that provide illumination for the image sensor, wherein the image sensor has a plurality of corners inserted into a wall of the camera cannula, and the plurality of light fibers are disposed in the wall of the camera cannula.

\* \* \* \* \*